US012716334B2

(12) United States Patent
Karimi et al.

(10) Patent No.: US 12,716,334 B2
(45) Date of Patent: Aug. 25, 2026

(54) METHODS AND SYSTEMS FOR PRODUCING ORGANIC COMPOUNDS IN A SUBTERRANEAN ENVIRONMENT

(71) Applicant: CEMVITA FACTORY, INC., Houston, TX (US)

(72) Inventors: Tahereh Karimi, Houston, TX (US); Mojtaba Karimi, Houston, TX (US)

(73) Assignee: CEMVITA FACTORY, INC., Houston, TX (US)

( * ) Notice: Subject to any disclaimer, the term of this patent is extended or adjusted under 35 U.S.C. 154(b) by 0 days.

(21) Appl. No.: 17/632,717

(22) PCT Filed: Aug. 20, 2020

(86) PCT No.: PCT/US2020/047250
§ 371 (c)(1),
(2) Date: Feb. 3, 2022

(87) PCT Pub. No.: WO2021/035076
PCT Pub. Date: Feb. 25, 2021

(65) Prior Publication Data

US 2022/0282604 A1 Sep. 8, 2022

Related U.S. Application Data

(60) Provisional application No. 62/889,977, filed on Aug. 21, 2019.

(51) Int. Cl.

| | |
|---|---|
| ***E21B 43/16*** | (2006.01) |
| ***C09K 8/582*** | (2006.01) |
| ***C09K 8/594*** | (2006.01) |
| ***C12P 5/02*** | (2006.01) |
| ***C12P 7/04*** | (2006.01) |
| ***C12P 7/06*** | (2006.01) |
| ***C12P 7/46*** | (2006.01) |
| ***C12P 7/54*** | (2006.01) |
| ***E21B 49/08*** | (2006.01) |
| *E21B 41/00* | (2006.01) |

(52) U.S. Cl.
CPC .............. *E21B 43/16* (2013.01); *C09K 8/582* (2013.01); *C09K 8/594* (2013.01); *C12P 5/02* (2013.01); *C12P 5/023* (2013.01); *C12P 5/026* (2013.01); *C12P 7/04* (2013.01); *C12P 7/06* (2013.01); *C12P 7/46* (2013.01); *C12P 7/54* (2013.01); *E21B 49/0875* (2020.05); *E21B 41/0064* (2013.01)

(58) Field of Classification Search
CPC ... E21B 41/0064; E21B 49/0875; C09K 8/58; C09K 8/582; C09K 8/594
See application file for complete search history.

(56) References Cited

U.S. PATENT DOCUMENTS

| | | | | |
|---|---|---|---|---|
| 4,446,919 | A * | 5/1984 | Hitzman | C09K 8/594 166/402 |
| 2001/0045279 | A1 | 11/2001 | Converse et al. | |
| 2004/0033557 | A1* | 2/2004 | Scott | C09K 8/62 435/132 |
| 2006/0254765 | A1* | 11/2006 | Pfeiffer | E21B 43/25 166/252.3 |
| 2008/0245672 | A1 | 10/2008 | Little et al. | |
| 2009/0325271 | A1 | 12/2009 | Upreti et al. | |
| 2010/0120104 | A1* | 5/2010 | Reed | C12P 5/023 435/166 |
| 2011/0281333 | A1* | 11/2011 | Brown | C12N 11/14 435/252.1 |
| 2011/0300411 | A1 | 12/2011 | Materi | |
| 2012/0003705 | A1 | 1/2012 | Jin et al. | |
| 2012/0115201 | A1* | 5/2012 | Adams | C10L 1/026 435/257.1 |
| 2013/0059358 | A1* | 3/2013 | Downey | E21B 43/006 435/167 |
| 2013/0068462 | A1* | 3/2013 | Pantano | E21B 43/164 166/305.1 |
| 2016/0145978 | A1* | 5/2016 | Theodore | C09K 8/582 166/246 |
| 2016/0290132 | A1 | 10/2016 | Knight et al. | |
| 2016/0319643 | A1* | 11/2016 | Lambourne | C09K 8/582 |
| 2017/0218740 | A1* | 8/2017 | Pichach | E21B 43/16 |

FOREIGN PATENT DOCUMENTS

| | | | | |
|---|---|---|---|---|
| CN | 101981744 | A | 2/2011 | |
| FR | 2955335 | A1 * | 7/2011 | C09K 8/68 |
| KR | 20110075969 | A | 7/2011 | |
| WO | 2002034931 | A2 | 5/2002 | |
| WO | 2008128331 | A1 | 10/2008 | |
| WO | WO-2009149519 | A1 * | 12/2009 | C12M 21/02 |

(Continued)

OTHER PUBLICATIONS

Translation of WO-2016151078-A1 (Year: 2016).*
Translation of FR 2955335 A1 Year: 2011.*
International Preliminary Report on Patentability of Application No. PCT/US2020/047250 mailed Mar. 3, 2022.
International Search Report and Written Opinion dated Nov. 19, 2020.
Yarbrough H F, Coty V E. Microbially enhanced oil recovery from the Upper Cretaceous Nacatoch formation, Union County Ark. Proceedings of International Conference on Microbial Enhancement of Oil Recovery, USA; 1983, p. 149-153.

(Continued)

*Primary Examiner* — Angela M DiTrani Leff
(74) *Attorney, Agent, or Firm* — Meunier Carlin & Curfman LLC

(57) ABSTRACT

Methods of producing organic compounds in a subterranean environment, and systems for the practice thereof are disclosed. A benefit of the methods disclosed herein can include cost-effectively converting a carbon dioxide feedstock stored in a subterranean environment into one or more organic compounds.

20 Claims, No Drawings

(56) References Cited

FOREIGN PATENT DOCUMENTS

| | | | | | |
|---|---|---|---|---|---|
| WO | 2014196481 | A1 | | 12/2014 | |
| WO | WO-2016151078 | A1 | * | 9/2016 | ............. B01D 53/62 |

OTHER PUBLICATIONS

Portwood J T (Company Alpha Environmental Midcontinent, Inc.). A commercial microbial enhanced oil recovery technology: Evaluation of 322 projects. Proceedings of the SPE Production Operations Symposium; Apr. 2-4, Oklahoma City, Okla.: SPE; 2007, p. 693-709.

* cited by examiner

METHODS AND SYSTEMS FOR PRODUCING ORGANIC COMPOUNDS IN A SUBTERRANEAN ENVIRONMENT

TECHNICAL FIELD

The present disclosure relates to methods of producing organic compounds in a subterranean environment, and systems for the practice thereof. A benefit of the methods disclosed herein can include the use of carbon dioxide stored in a subterranean environment to produce one or more organic compounds useful as fuel and feedstocks for other applications. Another benefit of the methods and systems disclosed herein can include reduction of excess carbon dioxide from the environment.

BACKGROUND

The world's population is estimated to be 7.7 billion and growing fast. These people all have at least one thing in common. They all inhale oxygen and exhale carbon dioxide. Also, they tend to increase the world's appetite for power and energy demand. This situation has created a strong demand for fossil fuels, such as oil and gas, and an excess of carbon dioxide from burning the oil and gas which many are calling a global warming crisis.

On the fossil fuel side, oil and gas producers are finding ways to increase the output of hydrocarbon wells, including such treatments as hydrolytic fracturing, the addition of chemicals to improve hydrocarbon flow, and microbial enhanced oil recovery. Microbial enhanced oil recovery (MEOR) is a tertiary oil extraction technology that manipulates the activity of microbial populations to improve reservoir flow properties, which can increase well production or control souring. However, all current known methods merely improve the ability of oil and gas producers to remove hydrocarbons from wells. None of them produce more hydrocarbons in the well and therefore none of them are sustainable.

On the global warming side, industry is desperate to prevent carbon dioxide from entering the atmosphere. Carbon Capture, Utilization and Storage (CCUS) is a demanding field that helps to reduce carbon dioxide emission. Carbon Capture, Utilization, and Storage includes methods and technologies to remove $CO_2$ from the flue gas or directly from the atmosphere, followed by utilization and storage in a safe site where it does not enter the atmosphere, which is normally underground, such as in a geological formation or other subterranean environment.

However, currently known methods just remove carbon dioxide from the atmosphere by storing it under ground, or through surface utilization applications, which require the construction of capital-intensive infrastructures at a large scale.

There remains a need to produce hydrocarbons for energy and feedstocks. There remains a need to remove excess carbon dioxide from the atmosphere. There remains a need to convert carbon dioxide into oxygen and other useful feedstocks in an economic and efficient manner. There remains a need for methods that can integrate the processes of carbon dioxide capture, utilization and storage.

SUMMARY

Embodiments herein are directed to methods of producing organic compounds in a subterranean environment, and related systems for the practice thereof. In an embodiment, a method of producing at least one organic compound in a subterranean environment is disclosed. In various embodiments, the method includes providing a carbon dioxide feedstock, a microbial culture, and a microbial growth medium; and converting a portion of the carbon dioxide feedstock into the at least one organic compound by adding the carbon dioxide feedstock, the microbial culture, and the microbial growth medium to the subterranean environment. In certain embodiments, the carbon dioxide feedstock contains from about 1.0 volume percent to 100 volume percent carbon dioxide based on a total volume of the carbon dioxide feedstock.

In certain embodiments, the subterranean environment includes a wellbore, a well formation containing a hydrocarbon, a natural cavern, a subterranean formation, an underground storage tank, or a combination thereof.

In various embodiments, the microbial culture includes at least one bacterial population native to the subterranean formation, at least one exogenous bacterial population, at least one anaerobic bacterial population, at least one genetically modified bacterial population, or a combination thereof. In certain embodiments, the microbial culture includes a *Geobacter* bacterium, a *Clostridium* bacterium, or a combination thereof. In certain embodiments, the microbial culture includes a *Bacillus* bacterium, a *Geobacillus* bacterium, a *Petrobacter* bacterium, a *Desulfotomaculum* bacterium, a *Bacteroides* bacterium, a *Thermoanaerobacter* bacterium, a *Thermococcus* bacterium, a *Thermotogales* bacterium, a *Petrotoga* bacterium, a *Thermotoga* bacterium, a *Desulfotomaculum* bacterium, a *Caminicella* bacterium, a *Geosporobacter* bacterium, or a combination thereof. In certain embodiments, the microbial culture includes, a methanotrophic bacterium, a methanogenic bacterium, an archaebacterium, a chemotrophic bacterium, n iron oxidizing bacterium, a sulfur oxidizing bacterium, an extremophile bacterium, a thermophilic bacterium, a halophilic bacterium, a hydrogen producing bacterium, a surfactant producing bacterium, an acetogenic bacterium, or a combination thereof.

In certain embodiments, the microbial growth medium is an aqueous liquid including from about 1 weight percent to 50 weight percent of at least one bio-based material, based on a total weight of the microbial growth medium. In certain embodiments, the at least one bio-based material includes glucose, fructose, glycerol, sucrose, maltodextrin, sodium chloride, a yeast extract, a malt extract, a casein peptone, sodium acetate, sodium lactate, a corn steep liquor, a watermelon rind, a corn cob, or combinations thereof.

In various embodiments, the at least one organic compound includes a $C_1$ to $C_{12}$ alkane, a $C_1$ to $C_4$ alcohol, a $C_1$ to $C_3$ organic acid, a $C_1$ to $C_{120}$ hydrocarbon, or a combination thereof. In certain embodiments, the at least one organic compound includes an alkane, methane, butane, pentane, hexane, heptane, octane, nonane, decane, deodecane, tetradecane, octadecane, an alkene, an alcohol, methanol, ethanol, propanol, butanediol, an organic acid, acetic acid, oxalic acid, an olefin, ethylene, a bio-surfactant, or a combination thereof.

In certain embodiments, the method includes harvesting at least one organic compound from the subterranean environment after a time period sufficient for the microbial culture to convert the portion of the carbon dioxide feedstock into the at least one organic compound. In certain embodiments, the method includes adding a second portion of carbon dioxide feedstock to the subterranean environment.

In certain embodiments, the method includes adding the carbon dioxide feedstock, the microbial culture, and the microbial growth medium to the subterranean environment, simultaneously, or in any order. In certain embodiments, the method includes injecting or pumping at least one of the carbon dioxide feedstock, the microbial culture and the microbial growth medium into the subterranean environment, simultaneously or in any order. In certain embodiments, the method includes injecting the microbial culture and the microbial growth medium together into the subterranean environment in a combined volume at an injection rate and an injection pressure sufficient to convert the portion of carbon dioxide feedstock into the at least one organic compound. In certain embodiments, the method includes forming a culture mixture by mixing the microbial culture and the microbial growth medium together; and adding the culture mixture and the carbon dioxide feedstock to the subterranean environment, simultaneously or in any order.

In certain embodiments, the method includes adding the carbon dioxide feedstock to a first subterranean environment, wherein the microbial culture and the microbial growth medium are added to a second subterranean environment, and wherein the first subterranean environment is connected to the second subterranean environment.

Certain embodied methods herein include collecting a first sample from a subterranean environment at a first time point; analyzing the first sample to obtain a first sample microbiome information; and selecting the microbial culture and the microbial growth medium based on the microbiome information of the first sample. Certain embodiments include selecting the microbial culture and the microbial growth medium based on at least one property of the subterranean environment, wherein the at least one property includes temperature, pressure, permeability, porosity, salinity, acidity, or combinations thereof. Certain embodiments include collecting a second sample from the subterranean environment at a second time point; analyzing the second sample to obtain a second sample microbiome information; selecting an adjustment dose based on the second sample microbiome information, wherein the adjustment dose includes a second microbial culture, a second microbial growth medium, or a combination thereof; and injecting the adjustment dose into the subterranean environment. In certain embodiments, the method includes measuring an amount of the at least one organic compound produced by at least one of the first microbial culture and the second microbial culture.

In certain embodiments, the method includes introducing at least one of an electrolysis apparatus and a hydrogen feedstock into the subterranean environment, wherein the hydrogen feedstock contains from about 1.0 volume percent to about 80 volume percent hydrogen based on a total volume of the gas feedstock.

Systems for producing at least one organic compound in a subterranean environment are disclosed herein. Certain embodiments of systems include a microbial culture vessel connected to a microbe injection port and a microbial growth medium vessel connected to a microbial growth medium injection port. Certain embodiments of systems include a culture mixture vessel connected to a culture mixture port. Various embodiments of systems include a supply pipeline connected to at least one of the microbe injection port, the microbial growth medium injection port, the culture mixture port, and to a pumping station; and an injection pipeline connected to the pumping station, wherein a portion of the injection pipeline is connected to the subterranean environment.

Methods for increasing the production of a hydrocarbon from a wellbore are disclosed herein. Embodiments of such methods include collecting a sample from a wellbore environment at a time point; analyzing the sample to obtain a sample microbiome information; selecting a microbial culture and a microbial growth medium based on the sample microbiome information, wherein the sample microbiome information comprises an adaptation of the microbial culture to at least one property of the wellbore environment, a resistance of the microbial culture to at least one property of the wellbore environment, at least one property of the wellbore environment, or a combination thereof; wherein the at least one property includes temperature, pressure, permeability, porosity, salinity, acidity, or combinations thereof; providing a biosurfactant feedstock; converting a portion of the biosurfactant feedstock into at least one biosurfactant and degrading at least one petroleum hydrocarbon, at least one paraffin, or combination thereof present in the wellbore environment by adding the biosurfactant feedstock, the microbial culture, and the microbial growth medium to the wellbore environment; wherein the microbial culture comprises a surfactant producing bacterium, a petroleum hydrocarbon degrading bacterium, a paraffin degrading bacterium, *Gordina* sp., *Pseudomonas* sp., *Bacillus* sp., *Bacillus subtilis*, a rock degrading bacterium, *Rhodothermus marinus*, or combinations thereof; and increasing production of the hydrocarbon from the wellbore.

DETAILED DESCRIPTION

Unless otherwise noted, all measurements are in standard metric units.

Unless otherwise noted, all instances of the words "a," "an," or "the" can refer to one or more than one of the word that they modify.

Unless otherwise noted, the phrase "at least one" means one or more than one of an object. For example, "at least one of the first microbial culture and the second microbial culture" means the first microbial culture, or more than one of the first microbial culture, or the second microbial culture, or more than one of the second microbial culture, or any combination thereof.

Unless otherwise noted, the term "about" refers to ±10% of the non-percentage number that is described, rounded to the nearest whole integer. For example, about 100 mm, would include 90 to 110 mm. Unless otherwise noted, the term "about" refers to ±5% of a percentage number. For example, about 50 weight percent would include 45 weight percent to 55 weight percent. When the term "about" is discussed in terms of a range, then the term refers to the appropriate amount less than the lower limit and more than the upper limit. For example, from about 50 weight percent to 100 weight percent would include from 45 weight percent to 100 weight percent.

Unless otherwise noted, properties (height, width, length, ratio etc.) as described herein are understood to be averaged measurements.

Unless otherwise noted, the terms "provide", "provided" or "providing" refer to the supply, production, purchase, manufacture, assembly, formation, selection, configuration, conversion, introduction, addition, or incorporation of any element, amount, component, reagent, quantity, measurement, or analysis of any method or system of any embodiment herein.

Unless otherwise noted, the term "carbon dioxide feedstock" refers to a gas containing an enhanced level of carbon dioxide that is greater than an atmospheric level of carbon dioxide.

Carbon dioxide emissions resulting from the use of fossil fuels continue to rise on a global scale. Reduction of atmospheric carbon dioxide levels is a key to mitigating or reversing climate change. One conventional way of reducing carbon dioxide in the atmosphere is to sequester carbon dioxide underground through enhanced oil recovery (EOR) processes. For example, millions of tons of carbon dioxide are injected into oil and gas reservoirs each year. Natural sources of carbon dioxide are commonly used in EOR operations, but carbon dioxide from industrial sources can also be used. Carbon capture and storage (CCS) is a prominent technology for removal of industrial carbon dioxide from the atmosphere. Carbon dioxide that is captured from refining and other industrial processes can be transported and stored in subterranean environments, such as former oil and gas fields, underground formations, un-mineable coal seams, natural caverns, deep saline reservoirs, and underground storage tanks. It has been estimated that over 20 trillion tons of carbon dioxide can potentially be stored in geological formations. CCS is a cost effective and affordable way to reduce carbon dioxide emissions, compared to other available methods. However, the carbon dioxide is merely being stored underground until it escapes. Therefore, this method is not a sustainable solution to excess carbon dioxide in the atmosphere. Also, there is little financial incentive for industries to pump carbon dioxide into subterranean environments unless forced to by environmental regulations or paid to as part of their business model. Arguably, global warming is a crisis because it is more lucrative to produce carbon dioxide than to dispose of carbon dioxide.

There remains a need for methods that can harness the abundance of industrial carbon dioxide for use in applications and products that are beneficial to the environment and industry.

Conventional methods have been developed to use microbes to increase the production of oil and gas from subterranean environments. Usually, the technologies make use of microbial activity to enhance production of oil and gas from subterranean environments by, for example, decreasing the viscosity of heavy oils for easy recovery. Historically, however, these methods have been a curiosity and have not been widely adopted.

Methods of increasing oil and gas production using microbial activity must address a number of practical problems. The preparation of suitable microorganisms that are highly active under the specific conditions of the reservoir need to take the composition and properties of the crude oil into account. Most of the microorganisms that can adapt to the conditions of the field may have little effect on the composition and properties of the crude oils, however. Industrial applications require new strains of microorganisms that are tolerant to high temperatures and saline concentrations, and that are also capable of synthesizing the desired surfactants, polysaccharides, biofuels, long chain carbohydrates, and other desired compounds. Another challenge is to establish techniques to create appropriate reservoir conditions that favor the growth and activity of specific microorganisms. This requires further exploration of ways to introduce additional nutrients, including nitrogen and phosphorus compounds. Another challenge is the development of cost-effective methods for sulfate reduction. Reservoir conditions are ecological niches for sulfate-reducing bacteria. It is often necessary to control the generation of hydrogen sulfide, because it creates the problems of a toxic aggressive environment, corrosion, higher sulfur content in the crude oil, toxic products, and other undesirable consequences.

Despite these challenges, along with the increased demand for fossil fuels, there is a growing emphasis on maximizing output from existing resources and developing sustainable sources of fuel, while minimizing environmental impacts. Plus, recent developments in cost-effective high throughput genetic sequencing technologies have led to an increased understanding of microbial communities native to subterranean environments. There is a growing inventory of microbial population data from subterranean environments, which is leading to wider use of microbes in the removal of hydrocarbons from subterranean environments. However, none of the known methods convert carbon dioxide into oxygen or any useful feed stocks. Instead, the conventional methods focus on using microbes for thoroughly and cost-effectively removing hydrocarbons from subterranean environments.

Embodiments of the present disclosure can provide methods that remove excess carbon dioxide from the atmosphere by storing it in a subterranean environment and using microbes to convert the carbon dioxide back into oxygen or a useful feedstock in the subterranean environment. That is, embodiments of the present disclosure can combine the carbon dioxide removal potential of conventional carbon dioxide sequestration methods with microbial technology to convert the carbon dioxide into oxygen or into at least one organic compound. For example, such methods could create renewable hydrocarbon wells by pumping existing carbon dioxide into subterranean environments along with microbes designed to transform that carbon dioxide into valuable organic compounds, such as hydrocarbons.

One benefit of the embodiments of the present disclosure is that the methods can make it economically profitable for an oil or natural gas company to remove carbon dioxide from the environment. An embodiment of the method and its economic efficiency can be illustrated by an example. An oil company discovers oil in a subterranean environment. The oil company pays to purchase the subterranean environment and pays to provide the infrastructure necessary to remove the oil from the subterranean environment using their standard operation procedures. Once the oil company has removed as much as much oil as possible from the subterranean environment, all that remains is a gigantic subterranean space that would typically be backfilled with water or the like to avoid sinkholes and environmental run off once the oil company moves to another site. Generally, the subterranean land is considered worthless, difficult to sell, and perhaps an environmental liability.

However, if the presently disclosed methods were used, then the oil company, or a contractor thereof, could fill the subterranean environment with carbon dioxide, a microbial culture, and a cost effective microbial growth medium, such as discarded corn husks and melon rinds. Then over time, the microbes could convert the carbon dioxide in the subterranean environment into at least one organic compound, such as ethanol or octane. The oil company could then return and use much of their old infrastructure to remove, refine, and sell the at least one organic compound. This process may be repeated indefinitely, giving the subterranean environment a sustainable value as a bioreactor. The methods disclosed herein can remove carbon dioxide from the environment and provide a valuable organic compound capable of being sold commercially. From an environmental standpoint, embodiments of the methods disclosed herein can provide refillable oil and gas wells that consume excess carbon dioxide and biowaste.

The most effective methods for protecting the environment are those methods that people actually use. The more profitable those methods are; the more likely people are to use them. One of the benefits of the methods disclosed herein is the cost-effectiveness of using a passive bioreactor system. In the example above, the oil company has already paid for the land, paid for all of the infrastructure necessary to pump materials into and out of the well, and profited from removing, refining, and selling the oil. There was no added step that might risk losing valuable hydrocarbon production. No new cost has been incurred to this point in the process. The oil well or subterranean environment can now be refilled by pumping a carbon dioxide feedstock, a microbial culture, and a microbial growth medium in the well at little cost as a final or near final step. Then, while the oil company moves onto the next drilling site, the microbes can convert the carbon dioxide feedstock and microbial growth medium into at least one organic compound. Sometime later, the oil company, or a contractor thereof, can return and remove the organic compounds and sell them for a profit. In this example, the vast majority of the expenses were incurred in removing the oil for sale. Refilling the well would require little more than excess carbon dioxide, biowaste, and time, all of which are readily available. Embodiments of the presently disclosed methods can make it profitable to remove carbon dioxide from the atmosphere and to passively generate valuable organic compounds while the microbes do the work—on a scale previously unimaginable.

What would happen to the global warming crisis if it became more profitable, or just as profitable, to convert carbon dioxide into valuable organic compounds as it did to generate the carbon dioxide in the first place? The presently disclosed methods might transform energy producers from global warming companies to global cooling companies.

Embodiments of the present disclosure can provide methods to produce at least one organic compound in a subterranean environment by providing a carbon dioxide feedstock, a microbial growth medium and a microbial culture in a subterranean environment, wherein the microbial culture converts a portion of the carbon dioxide feedstock into at least one organic compound. Embodiments herein can provide a benefit of the use of stored carbon dioxide gas as an abundant resource for the production of one or more organic compounds useful as fuels and for other applications.

Embodiments of Organic Compound Production Methods

Embodied methods as disclosed herein can include producing at least one organic compound in a subterranean environment. In various embodiments herein, the method includes providing a carbon dioxide feedstock, a microbial culture, and a microbial growth medium; and converting a portion of the carbon dioxide feedstock into the at least one organic compound. In an embodiment, the carbon dioxide feedstock, the microbial culture, and the microbial growth medium are added to the subterranean environment.

In an embodiment, the method includes adding the carbon dioxide feedstock, the microbial culture, and the microbial growth medium to the subterranean environment simultaneously. In an embodiment, the method includes adding the carbon dioxide feedstock, the microbial culture, and the microbial growth medium to the subterranean environment in any order. In an embodiment, the method includes injecting or pumping at least one of the carbon dioxide feedstock, the microbial culture and the microbial growth medium into the subterranean environment simultaneously. In an embodiment, the method includes injecting or pumping at least one of the carbon dioxide feedstock, the microbial culture and the microbial growth medium into the subterranean environment in any order. In an embodiment, the method includes forming a culture mixture by mixing the microbial culture and the microbial growth medium together; and adding the culture mixture and the carbon dioxide feedstock to the subterranean environment simultaneously. In an embodiment, the method includes forming a culture mixture by mixing the microbial culture and the microbial growth medium together; and adding the culture mixture and the carbon dioxide feedstock to the subterranean environment in any order. In an embodiment, the method includes injecting the microbial culture and the microbial growth medium together into the subterranean environment in a combined volume at an injection rate and an injection pressure sufficient to convert a portion of a carbon dioxide feedstock into at least one organic compound.

In an embodiment, the carbon dioxide feedstock is added to a first subterranean environment and the microbial culture and the microbial growth medium are added to a second subterranean environment, wherein the first subterranean environment is connected to the second subterranean environment. A benefit of such an embodiment can provide for using subterranean environments having gaseous or fluid connections, including but not limited to adjacent wells.

In an embodiment, the method includes harvesting the at least one organic compound from the subterranean environment after a time period sufficient for the microbial culture to convert a portion of the carbon dioxide feedstock into at least one organic compound. In an embodiment, a sufficient time period can include from about 1 year to about 20 years, including from about 5 years to about 15 years.

In an embodiment, the method can benefit from determining which microbes and/or microbial growth mediums are natural to or optimal for a subterranean environment. In an embodiment, the method includes collecting a first sample from the subterranean environment at a first time point; analyzing the first sample to obtain a first sample microbiome information; and selecting the microbial culture and the microbial growth medium based on the microbiome information of the first sample. In an embodiment, the method includes collecting a second sample from the subterranean environment at a second time point, analyzing the second sample to obtain a second sample microbiome information, and selecting an adjustment dose based on the second sample microbiome information. In some embodiments, the adjustment dose includes a second microbial culture, a second microbial growth medium, or a combination thereof. In an embodiment, the method includes injecting the adjustment dose into the subterranean environment.

In various embodiments, microbiome information can include, but is not limited to, microbial population information; a census of currently present microorganisms, living and nonliving; characterizations of microorganisms; genetic and biological material information; information derived from or ascertained from genetic material; fragments of genetic material or other biologic material, including DNA, RNA, protein, or carbohydrates; and metabolite profiles. Such embodiments can provide a benefit of selecting a microbial culture and a microbial growth medium to promote the survival and growth of the microbial culture in the subterranean environment, and the production of one or more organic compounds.

In an embodiment, the method includes measuring an amount of the at least one organic compound produced by at least one of the first microbial culture and the second microbial culture. In an embodiment, the method includes measuring an amount of carbon dioxide feedstock in the subterranean environment consumed by the at least one of the first microbial culture and the second microbial culture.

In an embodiment, a carbon dioxide feedstock can be injected or pumped into a subterranean formation using injection or pumping equipment that can also be used to inject or pump carbon dioxide into a subterranean formation for the purpose of increasing oil production. A benefit of such an embodiment can be a cost-effective use of injection or pumping equipment for the production of one or more organic compounds in a subterranean environment, and for the purpose of increasing oil production. Such an embodiment can provide a benefit of a cost-effective use of a subterranean formation for the purpose of oil production, and for the production of one or more organic compounds.

A carbon dioxide feedstock in various embodiments can include carbon dioxide gas from industrial emissions, carbon dioxide from a natural source, carbon dioxide captured from the atmosphere, carbon dioxide gas stored or injected into a subterranean environment, or combinations thereof. Such embodiments can provide a benefit of producing one or more useful organic compounds using a carbon dioxide feedstock including carbon dioxide from industrial emissions. Such embodiments can provide a benefit of a cost effective use of carbon dioxide from industrial sources for the production of organic compounds, in that revenue from the sale of the more one more organic compounds produced can be used to offset the cost of capturing and transporting the industrially produced carbon dioxide to the subterranean formation.

In some embodiments, the carbon dioxide feedstock contains from about 1.0 volume percent to 100 volume percent carbon dioxide based on a total volume of the carbon dioxide feedstock. In an embodiment, the carbon dioxide feedstock contains from about 2.0 volume percent to about 95 volume percent carbon dioxide or more based on a total volume of the carbon dioxide feedstock. In an embodiment, the carbon dioxide feedstock contains from about 5.0 volume percent to about 90 volume percent carbon dioxide or more based on a total volume of the carbon dioxide feedstock. In an embodiment, the method includes adding a second portion of carbon dioxide feedstock to the subterranean environment.

An embodiment of the method of producing at least one organic compound in a subterranean environment can benefit from a step of actively converting or facilitating the reaction of carbon dioxide feedstock into at least one organic material. In an embodiment, the method includes introducing at least one of an electrolysis apparatus and/or a hydrogen feedstock into the subterranean environment. In an embodiment, the hydrogen feedstock contains from about 1.0 volume percent to about 80 volume percent hydrogen based on a total volume of the hydrogen feedstock or the gas feedstock. In an embodiment, the hydrogen feedstock contains from about 2 volume percent to about 8 volume percent hydrogen based on a total volume of the hydrogen feedstock. In an embodiment, the hydrogen feedstock contains from about 4 volume percent to about 6 volume percent hydrogen based on a total volume of the hydrogen feedstock. A benefit of such an embodiment can include promoting the growth of the microbial culture and/or increasing the rate of conversion of carbon dioxide feedstock into at least one organic compound in the subterranean formation.

A subterranean environment in various embodiments can include a wellbore, a well formation containing a hydrocarbon, a natural cavern, a subterranean formation, an underground storage tank, or a combination thereof. In an embodiment, the method includes selecting the microbial culture and the microbial growth medium based on at least one property of the subterranean environment. In some embodiments, the at least one property of the subterranean environment includes temperature, pressure, permeability, porosity, salinity, acidity, or combinations thereof. In certain embodiments, the method includes selecting the microbial culture and the microbial growth medium based on an adaptation of the microbial culture to at least one property of the subterranean environment, selecting the microbial culture and the microbial growth medium based on a resistance of the microbial culture to at least one property of the subterranean environment, or a combination thereof.

Embodiments of microbial cultures herein can include at least one bacterial population native to the subterranean formation. A benefit of such embodiments can include selecting at least one bacterial population that is natively adapted to grow in the subterranean formation. In other embodiments, the microbial culture can include at least one exogenous bacterial population, or a combination of at least one native bacterial population and at least one exogenous bacterial population. In some embodiments, the microbial culture can include at least one anaerobic bacterial population, at least one genetically modified bacterial population, or a combination thereof. In an embodiment, at least one anaerobic bacterial population can include a *Geobacter* bacterium, a *Clostridium* bacterium, or a combination thereof. In certain embodiments, the microbial culture includes a *Bacillus* bacterium, a *Geobacillus* bacterium, a *Petrobacter* bacterium, a *Desulfotomaculum* bacterium, a *Bacteroides* bacterium, a *Thermoanaerobacter* bacterium, a *Thermococcus* bacterium, a *Thermotogales* bacterium, a *Petrotoga* bacterium, a *Thermotoga* bacterium, a *Desulfotomaculum* bacterium, a *Caminicella* bacterium, a *Geosporobacter* bacterium, or a combination thereof. In certain embodiments, the microbial culture includes a methanotrophic bacterium, a methanogenic bacterium, an archaebacterium, a chemotrophic bacterium, an iron oxidizing bacterium, a sulfur oxidizing bacterium, an extremophile bacterium, a thermophilic bacterium, a halophilic bacterium, a hydrogen producing bacterium, a surfactant producing bacterium, an acetogenic bacterium, or a combination thereof.

In various embodiments, the at least one microbial culture can be selected based on one or more properties of the subterranean environment. In such embodiments, the one or more properties of the subterranean environment can include temperature, pressure, permeability, porosity, salinity, acidity, or combinations thereof. Such embodiments can provide a benefit of selecting at least one bacterial population that is adapted to grow and convert a portion of the carbon dioxide feedstock into at least one organic compound in the subterranean environment.

Embodiments of microbial growth media herein can include an aqueous liquid. In various embodiments, materials that can be included in such an aqueous liquid can be selected to support the growth of the desired microorganisms. Such an aqueous liquid can include organic materials, including but not limited to materials such as yeast extract, extracts of animal origin such as beef extract and tryptone, agar, and vitamins. Such an aqueous liquid can also include inorganic materials, including but not limited to ammonium salts, carbonate salts, nitrates, phosphates, sodium chloride, and minerals. Examples of microbial growth media containing organic and inorganic materials include but are not limited to nutrient agar and Lysogeny Bertani (LB) broth.

Embodiments of microbial growth media including an aqueous liquid can include from about 1 weight percent to 50 weight percent of at least one bio-based material, based on a total weight of the microbial growth medium. In an embodiment, the aqueous liquid includes from about 10 weight percent to about 40 weight percent of at least one bio-based material. In an embodiment, the aqueous liquid includes from about 20 weight percent to about 30 weight percent of at least one bio-based material. In an embodiment, the aqueous liquid includes from about 1 weight percent to about 5 weight percent of at least one bio-based material. Embodiments of such an aqueous liquid can include an aqueous solution or slurry containing the at least one bio-based material. In an embodiment, the at least one bio-based material includes glucose, fructose, glycerol, sucrose, maltodextrin, sodium chloride, a yeast extract, a malt extract, a casein peptone, sodium acetate, sodium lactate, a corn steep liquor, a watermelon rind, a corn cob, molasses, a dry bio-based material, or combinations thereof. A benefit of such an embodiment can include the use of an abundant and cost-effective bio-based material in the microbial growth medium. Embodiments of microbial growth media including an aqueous liquid herein can provide a benefit of promoting the growth of the microbial culture in the subterranean environment. Another benefit of such an embodiment can be a microbial growth medium advantageous for injecting or pumping the microbial growth medium into a subterranean formation.

The at least one organic compound in various embodiments can include a $C_1$ to $C_{12}$ alkane, a $C_1$ to $C_4$ alcohol, a $C_1$ to $C_3$ organic acid, a $C_1$ to $C_{120}$ hydrocarbon, or a combination thereof. Examples of suitable hydrocarbons include an alkane, methane, butane, pentane, hexane, heptane, octane, nonane, decane, deodecane, tetradecane, octadecane, and combinations thereof. In some embodiments, the at least one organic compound can include an alkene, an alcohol, methanol, ethanol, propanol, butanediol, an organic acid, acetic acid, oxalic acid, an olefin, ethylene, a biosurfactant, or a combination thereof.

A benefit of the at least one organic compound in various embodiments can include the provision of at least one organic compound useful as a fuel, or for other useful applications.

Embodied methods disclosed herein can include methods for increasing the production of a hydrocarbon from a wellbore. In such an embodiment, the method can include collecting a sample from a wellbore environment at a time point; analyzing the sample to obtain a sample microbiome information; selecting a microbial culture and a microbial growth medium based on the sample microbiome information, wherein the sample microbiome information comprises an adaptation of the microbial culture to at least one property of the wellbore environment, a resistance of the microbial culture to at least one property of the wellbore environment, at least one property of the wellbore environment, or a combination thereof; wherein the at least one property includes temperature, pressure, permeability, porosity, salinity, acidity, or combinations thereof, providing a biosurfactant feedstock; converting a portion of the biosurfactant feedstock into at least one biosurfactant and degrading at least one petroleum hydrocarbon, at least one paraffin, or combination thereof present in the wellbore environment by adding the biosurfactant feedstock, the microbial culture, and the microbial growth medium to the wellbore environment; wherein the microbial culture comprises a surfactant producing bacterium, a petroleum hydrocarbon degrading bacterium, a paraffin degrading bacterium, *Gordina* sp., *Pseudomonas* sp., *Bacillus* sp., *Bacillus subtilis*, a rock degrading bacterium, *Rhodothermus marinus*, or combinations thereof, and increasing production of the hydrocarbon from the wellbore.

Embodied methods of increasing production of a hydrocarbon from a wellbore as disclosed herein, including embodiments producing at least one biosurfactant in a wellbore environment, can provide a benefit of enhancing Microbially Enhanced Oil Recovery (MEOR) processes. Embodiments providing a petroleum hydrocarbon degrading bacterium, a paraffin degrading bacterium, or combinations thereof can provide a benefit of degrading long chain hydrocarbons, including waxy hydrocarbons, which can lead to a decrease in the viscosity and an increase in the mobility of oil present in the wellbore environment, thus aiding an increase in production of a hydrocarbon from the wellbore. Embodiments providing a rock degrading bacterium can provide a benefit of degrading silicon-based rocks present in the wellbore environment, thus increasing the porosity of the rocks and aiding an increase in hydrocarbon recovery.

Systems of Various Embodiments

Embodiments of systems disclosed herein can include a system for producing at least one organic compound in a subterranean environment. In an embodiment, the system includes a microbial culture vessel connected to a microbe injection port and a microbial growth medium vessel connected to a microbial growth medium injection port. In an embodiment, the system includes a microbial culture mixture vessel connected to a culture mixture port. In an embodiment, the system includes a supply pipeline connected to at least one of a microbe injection port, a microbial growth medium injection port, and a culture mixture port. In various embodiments, the supply pipeline and an injection pipeline are connected to a pumping station, wherein a portion of the injection pipeline is connected to the subterranean environment. In an embodiment, a carbon dioxide feedstock can be injected or pumped into a subterranean formation using a supply pipeline, an injection pipeline, a pumping station, or a combination thereof, wherein the supply pipeline, the injection pipeline, the pumping station, or combination thereof can also be used to inject or pump carbon dioxide into a subterranean formation for the purpose of increasing oil production in an EOR process. Such an embodiment can provide a benefit of a cost-effective use of equipment for the production of one or more organic compounds in a subterranean environment, as well as for increasing oil production. Such an embodiment can provide a benefit of a cost-effective use of a subterranean formation for the purpose of oil production and for the production of one or more organic compounds.

EXAMPLES

Example 1

In a method of producing at least one organic compound in a subterranean environment, a first sample is collected from the subterranean environment at a first time point. The first sample is analyzed to obtain a first sample microbiome information. Based on the first sample microbiome information, a microbial culture native to the subterranean environment, including a *Geobacter* culture, and a suitable microbial growth medium. The microbial culture and the microbial growth medium are selected further based on at least one property of the subterranean environment (temperature, pressure, permeability, porosity, salinity, acidity, or combinations thereof). A carbon dioxide feedstock containing 80 volume percent carbon dioxide is provided in the subterranean environment. A selected microbial culture is provided in a microbial culture vessel, and a selected microbial growth medium is provided in a microbial growth medium vessel. The microbial culture and the microbial growth medium are injected simultaneously, respectively through a microbe injection port and a microbial growth medium injection port, into a supply pipeline. The supply pipeline and an injection pipeline are connected to a pumping station; the injection pipeline is connected to the subterranean environment. The microbial culture and the microbial growth medium are pumped through the supply pipeline and the injection pipeline into the subterranean environment. At a second time point, a second sample is collected from the subterranean environment and analyzed to obtain a second sample microbiome information. Based on the second sample microbiome information, an adjustment dose is selected, including a second microbial culture and a second microbial growth medium. The adjustment dose is injected into the subterranean environment. The amount of the at least one organic compound produced by the microbial culture is periodically measured. After a time period sufficient for the microbial culture to convert a portion of the carbon dioxide feedstock into at least one organic compound, the at least one organic compound is harvested from the subterranean environment.

Example 2

In a method of producing at least one organic compound in a subterranean environment, prior to the application of MEOR technologies, the projects are assessed to determine the compatibility of the crude oil and reservoir properties with MEOR, taking into account the physicochemical properties of the crude oil, reservoir production performance, and reservoir properties, including temperature. At the preliminary stage, reservoir fluid samples are collected and tested for compatibility with the MEOR systems. The first stage is the identification of the indigenous hydrocarbon-consuming bacteria, which are already adapted to the in situ reservoir conditions; after which the best action strategy for each project is designed and developed. MEOR methods for enhancement of oil recovery from subterranean formations are disclosed in Yarbrough H F, Coty V E. Microbially enhanced oil recovery from the Upper Cretaceous Nacatoch formation, Union County Ark. *Proceedings of International Conference on Microbial Enhancement of Oil Recovery*, USA; 1983, p. 149-153; and in Portwood J T (Company Alpha Environmental Midcontinent, Inc.). A commercial microbial enhanced oil recovery technology: Evaluation of 322 projects. *Proceedings of the SPE Production Operations Symposium;* 2-4 April, Oklahoma City, Okla.: SPE; 2007, p. 693-709.

MEOR techniques are applied on individual wells as follows: (1) from the well being treated or (2) from the target well and adjacent wells of the same reservoir. The MEOR solution is injected into adjacent wells in the same way as water is injected into the reservoir. The volume of the MEOR biomaterial to be injected is calculated based on the pore volume of the target reservoir. The solution is mixed and pumped through the injection well followed by the injection of water to drive the biological solution into the oil saturated zones. Then, the treated well is shut in for the required period of time (normally 24 hours to 7 days), after which oil production is resumed. This procedure is repeated every 3-6 months to enable microorganisms to move deeper into the deposit to oil saturated zones.

EXEMPLARY EMBODIMENTS

Embodiment 1. A method of producing at least one organic compound in a subterranean environment comprising:

providing a carbon dioxide feedstock, a microbial culture, and a microbial growth medium; and converting a portion of the carbon dioxide feedstock into the at least one organic compound by adding the carbon dioxide feedstock, the microbial culture, and the microbial growth medium to the subterranean environment, wherein the carbon dioxide feedstock contains from about 1.0 volume percent to 100 volume percent carbon dioxide based on a total volume of the carbon dioxide feedstock.

Embodiment 2. The method of Embodiment 1, wherein the subterranean environment includes a wellbore, a well formation containing a hydrocarbon, a natural cavern, a subterranean formation, an underground storage tank, or a combination thereof Embodiment 3. The method of any of the above Embodiments 1-2, wherein the microbial culture includes at least one bacterial population native to the subterranean formation, at least one exogenous bacterial population, at least one anaerobic bacterial population, at least one genetically modified bacterial population, or a combination thereof Embodiment 4. The method of any of the above Embodiments 1-3, wherein the microbial culture includes a *Geobacter* bacterium, a *Clostridium* bacterium, a *Bacillus* bacterium, a *Geobacillus* bacterium, a *Petrobacter* bacterium, a *Desulfotomaculum* bacterium, a *Bacteroides* bacterium, a *Thermoanaerobacter* bacterium, a *Thermococcus* bacterium, a *Thermotogales* bacterium, a *Petrotoga* bacterium, a *Thermotoga* bacterium, a *Desulfotomaculum* bacterium, a *Caminicella* bacterium, a *Geosporobacter* bacterium, or a combination thereof; or the microbial culture includes a methanotrophic bacterium, a methanogenic bacterium, an archaebacterium, a chemotrophic bacterium, an iron oxidizing bacterium, a sulfur oxidizing bacterium, an extremophile bacterium, a thermophilic bacterium, a halophilic bacterium, a hydrogen producing bacterium, a surfactant producing bacterium, an acetogenic bacterium, or a combination thereof.

Embodiment 5. The method of any of the above Embodiments 1-4, wherein the microbial growth medium is an aqueous liquid including from about 1 weight percent to 50 weight percent of at least one bio-based material, based on a total weight of the microbial growth medium.

Embodiment 6. The method of any of the above Embodiment 5, wherein the at least one bio-based material includes glucose, fructose, glycerol, sucrose, maltodextrin, sodium chloride, a yeast extract, a malt extract, a casein peptone, sodium acetate, sodium lactate, a corn steep liquor, a watermelon rind, a corn cob, molasses, a dry bio-based material, or combinations thereof Embodiment 7. The method of any of the above Embodiments 1-6, wherein the at least one organic compound includes a C1 to C12 alkane, a C1 to C4 alcohol, a C1 to C3 organic acid, a C1 to C120 hydrocarbon, or a combination thereof Embodiment 8. The method of any of the above Embodiments 1-7, wherein the at least one organic compound includes an alkane, methane, butane, pentane, hexane, heptane, octane nonane, decane, deodecane, tetradecane, octadecane, an alkene, an alcohol, methanol, ethanol, propanol, butanediol, an organic acid, acetic acid, oxalic acid, an olefin, ethylene, a bio-surfactant, or a combination thereof Embodiment 9. The method of any of the above Embodiments 1-8, further comprising, harvesting the at least one organic compound from the subterranean environment after a time period sufficient for the microbial culture to convert the portion of the carbon dioxide feedstock into the at least one organic compound; or adding a second portion of carbon dioxide feedstock to the subterranean environment.

Embodiment 10. The method of any of the above Embodiments 1-9, further comprising, collecting a first sample from the subterranean environment at a first time point; analyzing the first sample to obtain a first sample microbiome information; and selecting the microbial culture and the microbial growth medium based on the microbiome information of the first sample.

Embodiment 11. The method of any of the above Embodiments 1-10, further comprising, selecting the microbial culture and the microbial growth medium based on at least one property of the subterranean environment, wherein the at least one property includes temperature, pressure, permeability, porosity, salinity, acidity, or combinations thereof.

Embodiment 12. The method of Embodiment 11, further comprising, collecting a second sample from the subterranean environment at a second time point; analyzing the second sample to obtain a second sample microbiome information; selecting an adjustment dose based on the second sample microbiome information, wherein the adjustment dose includes a second microbial culture, a second microbial growth medium, or a combination thereof; and injecting the adjustment dose into the subterranean environment.

Embodiment 13. The method of Embodiment 12, further comprising, measuring an amount of the at least one organic compound produced by at least one of the first microbial culture and the second microbial culture.

Embodiment 14. The method of any of Embodiments 1-13 above, further comprising, adding the carbon dioxide feedstock, the microbial culture, and the microbial growth medium to the subterranean environment, simultaneously, or in any order; or injecting or pumping at least one of the carbon dioxide feedstock, the microbial culture and the microbial growth medium into the subterranean environment, simultaneously or in any order.

Embodiment 15. The method of any of Embodiments 1-14 above, further comprising, forming a culture mixture by mixing the microbial culture and the microbial growth medium together; and adding the culture mixture and the carbon dioxide feedstock to the subterranean environment, simultaneously or in any order.

Embodiment 16. The method of any of Embodiments 1-15 above, wherein the carbon dioxide feedstock is added to a first subterranean environment, wherein the microbial culture and the microbial growth medium are added to a second subterranean environment, and wherein the first subterranean environment is connected to the second subterranean environment.

Embodiment 17. The method of any of Embodiments 1-16 above, further comprising, injecting the microbial culture and the microbial growth medium together into the subterranean environment in a combined volume at an injection rate and an injection pressure sufficient to convert the portion of carbon dioxide feedstock into the at least one organic compound.

Embodiment 18. The method of any of Embodiments 1-17 above, further comprising, introducing at least one of an electrolysis apparatus and a hydrogen feedstock into the subterranean environment, wherein the hydrogen feedstock contains from about 1.0 volume percent to about 80 volume percent, based on a total volume of the gas feedstock.

Embodiment 18A. The method of any of Embodiments 1-17 above, further comprising, a. introducing at least one of an electrolysis apparatus and a hydrogen feedstock into the subterranean environment, wherein the hydrogen feedstock contains from about 1 volume percent to about 80 volume percent hydrogen based on a total volume of the hydrogen feedstock.

Embodiment 18B. The method of any of Embodiments 1-17 above, further comprising, introducing at least one of an electrolysis apparatus and a gas feedstock into the subterranean environment, wherein the gas feedstock contains from about 1 volume percent to about 80 volume percent hydrogen based on a total volume of the gas feedstock.

Embodiment 19. A system for producing at least one organic compound in a subterranean environment comprising:

a microbial culture vessel connected to a microbe injection port and a microbial growth medium vessel connected to a microbial growth medium injection port, or a culture mixture vessel connected to a culture mixture port;

a supply pipeline connected to at least one of the microbe injection port, the microbial growth medium injection port, the culture mixture port, and to a pumping station; and an injection pipeline connected to the pumping station, wherein a portion of the injection pipeline is connected to the subterranean environment.

Embodiment 20. A method for increasing the production of a hydrocarbon from a wellbore comprising:

collecting a sample from a wellbore environment at a time point;

analyzing the sample to obtain a sample microbiome information;

selecting a microbial culture and a microbial growth medium based on the sample microbiome information, wherein the sample microbiome information comprises an adaptation of the microbial culture to at least one property of the wellbore environment, a resistance of the microbial culture to at least one property of the wellbore environment, at least one property of the wellbore environment, or a combination thereof;

wherein the at least one property includes temperature, pressure, permeability, porosity, salinity, acidity, or combinations thereof;

providing a biosurfactant feedstock;

converting a portion of the biosurfactant feedstock into at least one biosurfactant and degrading at least one petroleum hydrocarbon, at least one paraffin, or combination thereof present in the wellbore environment by adding the biosurfactant feedstock, the microbial culture, and the microbial growth medium to the wellbore environment; wherein the microbial culture comprises a surfactant producing bacterium, a petroleum hydrocarbon degrading bacterium, a paraffin degrading bacterium, *Gordina* sp., *Pseudomonas* sp., *Bacillus* sp., *Bacillus subtilis*, a rock degrading bacterium, *Rhodothermus marinus*, or combinations thereof; and increasing production of the hydrocarbon from the wellbore.

What is claimed is:

1. A method of producing at least one organic compound in a subterranean environment comprising:

providing a carbon dioxide feedstock, a microbial culture, and a microbial growth medium; and converting a portion of the carbon dioxide feedstock into the at least one organic compound by adding the carbon dioxide feedstock, the microbial culture, and the microbial growth medium to the subterranean environment, wherein the carbon dioxide feedstock contains from about 1.0 volume percent to 100 volume percent carbon dioxide based on a total volume of the carbon dioxide feedstock; and further comprising the steps of:

collecting a first sample from the subterranean environment at a first time point;

analyzing the first sample to obtain a first sample microbiome information; and selecting the microbial culture and the microbial growth medium based on the microbiome information of the first sample to promote the survival and growth of the microbial culture in the subterranean environment, and the production of one or more organic compounds;

wherein the at least one organic compound includes methanol; and wherein the microbial culture includes a *Geobacter* bacterium, a *Clostridium* bacterium, a *Bacillus* bacterium, a *Geobacillus* bacterium, a *Petrobacter* bacterium, a *Desulfotomaculum* bacterium, a *Bacteroides* bacterium, a *Thermoanaerobacter* bacterium, a *Thermococcus* bacterium, a *Thermotogales* bacterium, a *Petrotoga* bacterium, a *Thermotoga* bacterium, a *Caminicella* bacterium, a *Geosporobacter* bacterium, or a combination thereof.

2. The method of claim 1, wherein the subterranean environment includes a wellbore, a well formation containing a hydrocarbon, a natural cavern, a subterranean formation, an underground storage tank, or a combination thereof.

3. The method of claim 1, wherein the microbial culture includes at least one bacterial population native to the subterranean environment, at least one exogenous bacterial population, at least one anaerobic bacterial population, at least one genetically modified bacterial population, or a combination thereof.

4. The method of claim 1, wherein the microbial culture includes a *Geobacter* bacterium.

5. The method of claim 1, wherein the microbial growth medium is an aqueous liquid including from about 1 weight percent to 50 weight percent of at least one bio-based material, based on a total weight of the microbial growth medium.

6. The method of claim 5, wherein the at least one bio-based material includes glucose, fructose, glycerol, sucrose, maltodextrin, sodium chloride, a yeast extract, a malt extract, a casein peptone, sodium acetate, sodium lactate, a corn steep liquor, a watermelon rind, a corn cob, molasses, a dry bio-based material, or combinations thereof.

7. The method of claim 1, wherein the at least one organic compound does not include methane.

8. The method of claim 1, further comprising, harvesting the at least one organic compound from the subterranean environment after a time period sufficient for the microbial culture to convert the portion of the carbon dioxide feedstock into the at least one organic compound; or adding a second portion of carbon dioxide feedstock to the subterranean environment.

9. The method of claim 1, further comprising, selecting the microbial culture and the microbial growth medium based on at least one property of the subterranean environment, wherein the at least one property includes temperature, pressure, permeability, porosity, salinity, acidity, or combinations thereof.

10. The method of claim 1, further comprising, collecting a second sample from the subterranean environment at a second time point; analyzing the second sample to obtain a second sample microbiome information;

selecting an adjustment dose based on the second sample microbiome information, wherein the adjustment dose includes a second microbial culture, a second microbial growth medium, or a combination thereof; and injecting the adjustment dose into the subterranean environment.

11. The method of claim 10, further comprising, measuring an amount of the at least one organic compound produced by at least one of the first microbial culture and the second microbial culture.

12. The method of claim 1, further comprising, adding the carbon dioxide feedstock, the microbial culture, and the microbial growth medium to the subterranean environment, simultaneously, or in any order; and/or injecting or pumping at least one of the carbon dioxide feedstock, or the microbial culture and the microbial growth medium, into the subterranean environment.

13. The method of claim 1, further comprising, forming a culture mixture by mixing the microbial culture and the microbial growth medium together; and adding the culture mixture and the carbon dioxide feedstock to the subterranean environment, simultaneously or in any order.

14. The method of claim 1, wherein the carbon dioxide feedstock is added to a first subterranean environment, wherein the microbial culture and the microbial growth medium are added to a second subterranean environment, and wherein the first subterranean environment is connected to the second subterranean environment.

15. The method of claim 1, further comprising, injecting the microbial culture and the microbial growth medium together into the subterranean environment in a combined volume at an injection rate and an injection pressure sufficient to convert the portion of carbon dioxide feedstock into the at least one organic compound.

16. The method of claim 1, further comprising, introducing at least one of an electrolysis apparatus and a hydrogen feedstock into the subterranean environment, wherein the hydrogen feedstock contains from about 1 volume percent to about 80 volume percent hydrogen based on a total volume of the hydrogen feedstock.

17. The method of claim 1, wherein the microbial culture further includes an archaebacterium, a chemotrophic bacterium, an iron oxidizing bacterium, a sulfur oxidizing bacterium, an extremophile bacterium, a thermophilic bacterium, a halophilic bacterium, a hydrogen producing bacterium, a surfactant producing bacterium, an acetogenic bacterium, or a combination thereof.

18. The method of claim 1, wherein the microbial culture further comprises a surfactant producing bacterium, a petroleum hydrocarbon degrading bacterium, a paraffin degrading bacterium, *Gordina* sp, *Pseudomonas* sp., *Bacillus* sp., *Bacillus subtilis*, a rock degrading bacterium, *Rhodothermus marinus*, or combinations thereof.

19. The method of claim 1, wherein the at least one organic compound further includes butane, pentane, hexane, heptane, octane, nonane, decane, dodecane, tetradecane, octadecane, ethanol, propanol, butanediol, acetic acid, oxalic acid, ethylene, or a combination thereof.

20. The method of claim 1, wherein the carbon dioxide feedstock contains from about 2.0 volume percent to 95 volume percent carbon dioxide based on a total volume of the carbon dioxide feedstock.

* * * * *